United States Patent [19]

Rudzik

[11] 4,375,473

[45] Mar. 1, 1983

[54] METHOD

[75] Inventor: Allan D. Rudzik, Kalamazoo, Mich.

[73] Assignee: The Upjohn Company, Kalamazoo, Mich.

[21] Appl. No.: 336,797

[22] Filed: Jan. 4, 1982

[51] Int. Cl.³ .............................................. A61K 31/41
[52] U.S. Cl. ................................................... 424/269
[58] Field of Search ......................................... 424/269

[56] References Cited

U.S. PATENT DOCUMENTS

| | | | |
|---|---|---|---|
| 3,091,569 | 5/1963 | Sheffner | 424/319 |
| 3,422,091 | 1/1969 | Archer et al. | 260/239 BD |
| 3,709,898 | 1/1973 | Hester, Jr. | 260/245.5 |
| 3,879,413 | 4/1975 | Hester, Jr. | 260/245.5 |
| 3,980,789 | 9/1976 | Hester, Jr. | 424/269 |
| 3,980,790 | 9/1976 | Hester, Jr. | 424/269 |
| 3,987,052 | 10/1976 | Hester, Jr. | 260/245.5 |
| 4,000,289 | 12/1976 | Collins | 424/269 |

*Primary Examiner*—Jane T. Fan

[57] ABSTRACT

This specification concerns the use to treat hypertension in mammals of certain known 6-phenyl-4H-s-triazolo[4,3-a][1,4]benzodiazepines.

6 Claims, No Drawings

METHOD

The present invention relates to a novel method of use for known compounds.

In particular, the invention relates to the novel method of lowering the blood pressures of mammals, including humans, by administration thereto of sufficient amounts of certain known 6-phenyl-4H-s-triazolo[4,3-a][1,4]benzodiazepines or pharmacologically acceptable acid addition salts thereof.

The invention concerns, therefore, a method of treating hypertension in mammals, including humans.

Hypertension is a disease characterized by pathologically elevated, systemic arterial blood pressure. Hypertension in humans and agents for treating the disease have recently been reviewed by Comer and Matier in Burger's Medicinal Chemistry, 4th Ed., Part III, John Wiley and Sons, Inc., New York, 1981, pp. 285–337. Hypertension is also known to occur in non-human mammals. See, e.g., The Merck Veterinary Manual, 5th Ed., Merck and Co., Rahway, New Jersey, 1979, p. 59.

Ill effects caused or exacerbated by hypertension, in humans as well as other mammals, include renal insufficiency and failure, stroke, cardiac insufficiency and failure, and increased risks of coronary and cerebral atherosclerosis and the untoward consequences thereof. By reducing the blood pressure of a mammal suffering from hypertension, the ill effects of the disease can be prevented, ameliorated, or eliminated.

Numerous methods and agents for reducing blood pressure in mammals are known. Methods and agents for reducing hypertension in humans are reviewed in the Comer and Matier reference cited above. Most methods and agents effective for reducing hypertension in humans are also effective for reducing blood pressure in non-human mammals, including those suffering from hypertension. Indeed, the usefulness of a method or agent for treating hypertension in humans is usually first indicated by its blood-pressure lowering effect in non-human mammals.

Numerous agents active in the central nervous system are known to be antihypertensives. Many of these centrally acting agents are also active as hypnotics, sedatives, tranquilizers, or muscle relaxants. See the Comer and Matier chapter, cited above, at pages 292–302.

There are indications that non-triazole-ring-bearing benzodiazepines, such as diazepam and bromazepam, which are active through the central nervous systems of mammals as, among others, tranquilizers, muscle relaxants, sedatives, anxiolytics or anticonvulsants, might also be active as antihypertensives in mammals. See Chai et al., J. Pharm. Exp. Ther. 154, 271 (1966); Anonymous, Med. Lett. Drug Therap. 16, 96 (1974); Whitehead et al., Biol. Psych. 12, 597 (1977); D. Kelly, "Clinical Experience with Benzodiazepines in Psychosomatic Disorders," in R. G. Priest et al., eds., Benzodiazepines Today and Tomorrow, University Park Press, Baltimore, Maryland, 1980, pp. 99–112.

Known compounds of concern in the present specification are disclosed in Hester, J. Heterocyclic Chem. 17, 575 (1980); Hester and VonVoigtlander, J. Med. Chem. 22, 1390 (1979); Hester, Rudzik and Kamdar, J. Med. Chem. 14, 1078 (1971); and in U.S. Pat. Nos. 3,709,898; 3,879,413 and 3,987,052.

The known compounds are disclosed to be active as sedatives, tranquilizers and muscle relaxants in mammals and birds. See U.S. Pat. No. 3,987,052. They have also been disclosed to be useful for increasing the growth rate, productivity and feed-utilization efficiency of meat-producing, milk-producing or egg-laying farm animals. U.S. Pat. No. 4,000,289. One of the known compounds, 8-chloro-1-methyl-6-phenyl-4H-s-triazolo[4,3-a][1,4]benzodiazepine, has been disclosed to be a sleep-inducer in animals (U.S. Pat. No. 3,980,789), to possess anxiolytic activity in mammals (Hester and VonVoigtlander, cited above; Itil et al., Curr. Ther. Res. Clin. Exp. 15, 603 (1973)), and to display antidepressant activity in humans (L. F. Fabre et al., Curr. Ther. Res. 27, 474 (1980); L. F. Fabre., Curr. Ther. Res. 19, 661 (1976)). Another of the known compounds, 8-bromo-1-methyl-6-phenyl-4H-s-triazolo[4,3-a][1,4]benzodiazepine, also has been found to have anxiolytic activity in mammals. Hester and VonVoigtlander, cited above.

SUMMARY OF THE INVENTION

The present invention provides a method of treating hypertension in mammals which comprises administering to a mammal suffering from said disease an amount of a compound of formula I wherein $R_1$ is hydrogen or alkyl of 1 to 3 carbon atoms; wherein $R_4$ is hydrogen or methyl; and wherein $R_8$ is hydrogen or halogen; or a pharmacologically acceptable acid addition salt thereof, effective to reduce the mammal's systemic arterial blood pressure.

"Alkyl of 1 to 3 carbon atoms" means methyl, ethyl, n-propyl or isopropyl.

"Halogen" means fluorine, chlorine, bromine or iodine.

Methods for preparing the compounds of formula I are known. See Hester (1980) and Hester, Rudzik and Kamdar (1971), cited above, and U.S. Pat. Nos. 3,987,052; 3,879,413; 3,709,898 and 3,422,091.

A pharmacologically acceptable acid addition salt of the compounds of formula I can be made by reacting the free bases with the acid corresponding to the salt to be formed. The pharmacologically acceptable acid addition salts contemplated for the present invention include the hydrochlorides, hydrobromides, hydroiodides, sulfates, nitrates, phosphates, acetates, propionates, palmitates, benzoates, salicylates, hexynoates, phenylbutyrates, naphthoates, glycolates, succinates, nicotinates, tartrates, maleates, malates, pamoates, methanesulfonates, benzenesulfonates, toluenesulfonates, cyclohexanesulfonates, picrates, citrates, lactates, and the like.

Preferred compounds for use in the method of treatment disclosed herein are those wherein $R_4$ is hydrogen; $R_8$ is chloro, bromo or iodo; and $R_1$ is methyl, ethyl or n-propyl.

Most preferred are the preferred compounds wherein $R_1$ is methyl.

The method which comprises the present invention is to treat hypertension in mammals suffering therefrom. The invention is preferably applied to humans.

The skilled physician is able to ascertain by standard techniques when a human is suffering from hypertension, a disease characterized by a pathologically elevated, systemic arterial blood pressure. Hypertension in a human is indicated by a diastolic blood pressure (sitting) above about 85 mm Hg and a systolic blood pressure (sitting) above about 120 mm Hg. Diastolic blood pressure (sitting) above about 95 mm Hg and systolic blood pressure (sitting) above about 140 mm Hg are especially indicative of hypertension in a human.

The skilled veterinarian can ascertain when a non-human mammal is suffering from hypertension, i.e. pathologically elevated, systemic arterial blood pressure.

It is contemplated that, in carrying out the present invention, the compounds to which it pertains will be administered by any suitable route, including oral, parenteral, rectal, vaginal or transdermal. Accordingly, the pharmaceutical forms contemplated for carrying out the invention include pharmaceutical forms appropriate to these routes of administration, including tablets, capsules, powders and powder packets, cachets, dragees, solutions, suspensions, sterile injectable forms, suppositories, bougies, suspensions in membranes on tampons or other support means, and the like. In preparing these forms, the active compounds may be combined with suitable, pharmaceutically acceptable diluents or carriers such as carbohydrates (e.g., lactose or sucrose), proteins, lipids, calcium phosphate, cornstarch, stearic acid, methylcellulose, various oils (e.g., coconut, sesame, safflower, cottonseed, peanut or corn), water or aqueous solutions, or various polymeric membranes (e.g., polyvinylacetate films). Sweetening, coloring and flavoring agents may be added to the various formulations or used to coat the pharmaceutical forms.

The preferred route of administration is oral.

The method of treatment disclosed herein may be applied alone to treat a mammal suffering from hypertension or may be employed concomitantly or in conjunction with other methods for treating a mammal suffering from the disease, such as administration of other antihypertensive agents, dietary restrictions, and the like.

The dosage regimen for treating a mammal suffering from hypertension by the method of the present invention is determined in accordance with a variety of factors including the species, age, weight, sex, medical condition and severity of the hypertension of the mammal being treated, the particular compound or compounds being employed, the route of administration of such compound or compounds, and whether other methods for treating the mammal for hypertension are also employed. A skilled physician or veterinarian will readily ascertain and prescribe the correct amount of compound to be administered in carrying out the method of the present invention. In so doing, the physician or veternarian could employ relatively low dosages at first and subsequently increase dosages until the desired reduction in blood pressure is obtained.

For oral administration to a human, daily doses can vary from about 0.1 to about 100 mg per day of active compound in carrying out the method of the present invention. An equivalent dosage range for administration by other suitable routes may also be employed.

EXAMPLE 1

The hypotensive activity of compounds pertinent to the present invention was determined by tests on rats and baroreceptor-denervated cats:

A. Tests on Rats

Female Sprague-Dawley rats weighing 200–250 gm were fasted for 22–28 hours prior to anesthesia by intravenous (tail vein) administration of 8 ml/kg of a 5% glucose solution containing 5 mg/ml of α-chloralose, 5 mg/ml of urethane and 1.87 mg/ml of sodium pentobarbital.

Thirty minutes after anesthesia, the right external jugular vein and left common carotid artery were cannulated with PE-50 catheters, which had been pre-filled with 0.2 ml of 20 units/ml of heparanized saline.

Arterial pressures were continuously recorded through the arterial cannula with a Statham P23Gc transducer and Grass Model 7 polygraph.

All substances administered intravenously were administered through the venous cannula. Every intravenous administration of test compound of vehicle (N,N-dimethylacetamide) was followed by a rinse with 0.2 ml of 20 units/ml of heparanized saline.

The rats were affixed prone to test tube racks, one rat per rack, with 0 silk ligatures in their loose axillary skin. The racks were variably heated by passing warm water, at variable temperature and flow rate, through vinyl tubing passing through the racks. The rats were covered with aluminum foil domes and the heating was varied to maintain the rats' rectal temperatures between 34° and 37° C.

Sometime after the rats had been affixed to the racks and 90 minutes after administration of antesthetic, a 20 minute pre-treatment period was begun. During this period, the rats' arterial pressures stabilized to base-line values.

Following the 20 minute pre-treatment period, rats were dosed intravenously with vehicle alone (0.19 ml/kg of N,N-dimethylacetamide) as control or a test compound in vehicle. Vehicle control or test compound (dissolved in N,N-dimethylacetamide so that, to achieve the desired dose, 0.19 ml/kg of solution had to be administered) was administered cumulatively according to the following schedule:

| TIME (Post-treatment) min. | DOSE Vehicle Alone (control) ml/kg | DOSE Test Compound (in 0.19 ml of solution in vehicle) mg/kg |
|---|---|---|
| 0 | 0.19 | 0.03 |
| 20 | 0.19 | 0.3 |
| 40 | 0.19 | 3.0 |

For vehicle alone and each test compound, the procedure was applied to a group of at least four rats. For each such group, all rats were subjected to the procedure together, but the procedures started on individual rats 5–7 minutes apart.

For each rat, arterial pressures at 0 minute (just before first administration of vehicle or test compound), 20 minutes post-treatment (just before second administration of vehicle or test compound), 40 minutes post-treatment (just before third administration of vehicle or test compound), and 60 minutes post-treatment were determined. Thus, for each rat, the differences in arterial pressure at 20, 40, or 60 minutes post-treatment from that at 0 minutes could be determined. For each test compound and the vehicle alone as control, the average of each of these differences for all rats in the test or control group was determined. It is these averages, mean arterial pressure (MAP) changes, which were taken as the measure of the blood pressure-lowering effect of test compound (in vehicle) or vehicle alone and which are entered under "MAP Change" in Table A below.

Essentially the same procedure was applied with minoxidil (2,4-diamino-6-piperidinopyrimidine-3-oxide), a compound known to be an antihypertensive agent in humans. At post-treatment time 0, 3 to 5 mg/kg of minoxidil in 0.1 M citric acid as vehicle (1.0 ml/kg dose volume) was administered to the rats. At 15 minutes post-treatment, the arterial blood pressure of the rats was reduced 16±2 mm Hg, and at 30 minutes post-treatment their arterial blood pressure was reduced 19±3 mm Hg. In control rats, at post-treatment time 0 administered 1 ml/kg of 0.1 M citric acid, arterial blood pressure was reduced 4±1 mm Hg at 15 minutes and 6±1 mm Hg at 30 minutes post-treatment.

The procedure was also applied with clonidine (2-(2,6-dichloroanilino)-2-imidazoline), also a compound known to be an hypotensive agent in humans. At post-treatment time 0, 0.015 mg/kg of clonidine was administered in 0.9% sodium chloride as vehicle (0.5 ml/kg dose volume). At 15 minutes post-treatment, the arterial blood pressure of the rats was reduced 24±6 mm Hg, and at 30 minutes post-treatment their blood pressures were reduced 28±5 mm Hg. The aqueous sodium chloride vehicle alone was found to have no effect on the rats' blood pressure.

TABLE A

| Compound of Formula I (For each, $R_4$ is hydrogen) | | MAP Change (mm Hg) after | | |
|---|---|---|---|---|
| $R_1$ | $R_8$ | 0.03 mg/kg | plus 0.3 mg/kg | plus 3.0 mg/kg |
| H | Br | −6 | −15 | −20 |
| $CH_3$ | Cl | −2 | −13 | −23 |
| $CH_3$ | Br | −10 | −18 | −27 |
| n-$C_3H_7$ | Cl | −8 | −14 | −21 |
| $(CH_3)_2CH$ | Cl | −5 | −7 | −15 |
| | | 0.19 mg/kg | plus 0.19 mg/kg | plus 0.19 mg/kg |
| Control (N,N—dimethylacetamide) | | −5 | −6 | −7 |

B. Tests on Baroreceptor-denervated Cats

Compounds were tested for hypotensive activity in the baroreceptor-denervated cat. See, e.g., McCall et al., Europ. J. Pharmacol. 36, 69 (1976); McCall et al., J. Auton. Nerv. Sys. 3, 9 (1981).

Except as noted herein, the details of the procedure used are provided in the McCall et al. 1981 reference cited above.

Cats were anesthetized by i.p. injection of a mixture of diallyl barbiturate (60 mg/kg), urethane (240 mg/kg) and monoethylurea (240 mg/kg). The cats were then placed in a stereotaxic apparatus and were artificially respired with a Harvard respirator (50 cc×12 cpm). Arterial pressure was measured directly from a femoral artery cannula with a Statham transducer and a Grass polygraph. The cats were baroreceptor denervated by bilaterally sectioning the carotid sinus nerves, the vagi, and the aortic depressor nerves after everting the trachea and esophagus into the mouth. The external carotid nerve was isolated at its juncture with the superior cervical ganglion for monophasic recording of sympathetic discharges under oil with a platinum electrode. Acceptable nerve activity was not considered a prerequisite for inclusion into the study.

The cats were allowed to stabilize for a minimum of one hour following baroreceptor-denervation. After a 5-10 minute pre-treatment period, the cats were dosed intravenously with 0.03 mg/kg of a test compound. Subsequent to this initial dose, the drug was supplemented in a progressive, incremental fashion to total intravenous doses of 0.1, 0.3, 1.0, and 3.0 mg/kg at 30 minute intervals. The drug concentration for the first two dosages (0.03 mg/kg and 0.07 mg/kg) was 3.0 mg/ml in vehicle (N,N-dimethylacetamide). The drug concentration for the last three dosages (0.2 mg/kg, 0.7 mg/kg and 2.0 mg/kg) was 30.0 mg/ml in vehicle. Similarly prepared, untreated control cats received the vehicle alone in the following dosages: 0.01 ml/kg at post-treatment time 0, 0.023 ml/kg at post-treatment time 30 minutes, 0.007 ml/kg at post-treatment time one hour, 0.023 ml/kg at post-treatment time 1.5 hour, and 0.067 ml/kg at post-treatment time 2 hours.

Arterial pressure and integrated sympathetic nerve activity (SNA) were determined at 30 minutes after each administration of test compound or vehicle alone, just before a subsequent administration, if any, of test compound or vehicle.

Each mean arterial pressure change (MAP Change) reported in Table B is the average, for all cats in the group involved, of the differences between the arterial pressure at the time of measurement and that at post-treatment time 0. Similarly, each SNA reported in the Table is the average, for all cats in the group involved, of the percentage of activity at the time of measurement relative to that at post-treatment time 0.

TABLE B

| Compound of Formula I | | | | Dose | MAP Change | SNA (Relative to post-treatment |
|---|---|---|---|---|---|---|
| $R_1$ | $R_4$ | $R_8$ | $N^1$ | (Cumulative) | mm Hg | time 0, mean) % |
| | | | | mg/kg | | |
| $CH_3$ | H | Cl | 4 | 0.03 | −11 | −33 |
| | | | | 0.1 | −10 | −45 |
| | | | | 0.3 | −9 | −51 |
| | | | | 1.0 | −12 | −58 |
| | | | | 3.0 | −8 | −60 |
| $CH_3$ | H | Br | 4 | 0.03 | −9 | −38 |
| | | | | 0.1 | −34 | −57 |
| | | | | 0.3 | −33 | −58 |
| | | | | 1.0 | −37 | −60 |
| | | | | 3.0 | −20 | −63 |
| | | | | ml/kg | | |
| Vehicle (N,N—dimethylacetamide) | | | 7 | 0.01 | +6 | 0 |
| | | | | 0.033 | +6 | +15 |
| | | | | 0.04 | +6 | +24 |
| | | | | 0.063 | +4 | +35 |
| | | | | 0.13 | +3 | +34 |

[1]Number of cats used in test of compound

EXAMPLE 2

The hypotensive activity of 8-chloro-1-methyl-6-phenyl-4H-s-triazolo[4,3-a][1,4]benzodiazepine was also evaluated in humans as part of a multi-clinic, double-blind, placebo-controlled study of the compound's efficacy in the treatment of anxiety with associated hypertension. Volunteers who were subjects of the study (69 initially treated with the compound, 71 initially treated with placebo) suffered from mild to moderate symptoms of anxiety with associated hypertension.

The compound was administered orally via 0.25 mg tablets in a divided daily dose with a dosage range of 0.75 to 3.0 mg per day. Subjects receiving the compound received it daily for 12 weeks and then received placebo for 4 additional weeks. Blood pressures of all subjects were measured weekly through week 2 of the study and bi-weekly thereafter through week 16.

As indicated by the data in Table C, administration of the compound significantly reduced the mean blood pressure of the subjects receiving it.

TABLE C

| Week | | Number Evaluated | Mean Blood Pressure (sitting) mm Hg | | P-value of Difference from Mean at Week 0 | |
|---|---|---|---|---|---|---|
| | | | Systolic | Diastolic | Systolic | Diastolic |
| 0 | (F) | 25 | 157.2 | 98.5 | — | — |
| 0 | (M) | 41 | 154.4 | 97.3 | — | — |
| 1 | (F) | 25 | 145.0 | 94.2 | <0.001 | 0.015 |
| 1 | (M) | 41 | 149.4 | 94.7 | 0.023 | 0.032 |
| 4 | (F) | 25 | 140.3 | 88.4 | <0.001 | <0.001 |
| 4 | (M) | 41 | 145.1 | 92.5 | <0.001 | <0.0016 |
| 6 | (F) | 25 | 143.4 | 90.6 | 0.001 | <0.001 |
| 6 | (M) | 41 | 142.5 | 90.0 | <0.001 | <0.001 |
| 10 | (F) | 23 | 139.1 | 89.5 | <0.001 | <0.001 |
| 10 | (M) | 39 | 143.2 | 91.1 | 0.002 | <0.001 |
| 12 | (F) | 23 | 143.0 | 92.4 | 0.001 | 0.001 |
| 12 | (M) | 37 | 142.5 | 94.0 | <0.001 | 0.027 |
| 16 | (F) | 23 | 145.3 | 91.7 | 0.001 | 0.001 |
| 16 | (M) | 37 | 148.6 | 94.9 | 0.046 | 0.037 |

(F): Females
(M): Males

In the study, it was found that the mean blood pressure of placebo-treated subjects, male as well as female, also decreased significantly. In several instances, indicated in Table D, the mean blood pressure of compound-treated subjects was significantly lower than that of placebo-treated subjects. In no instance was the mean blood pressure of placebo-treated subjects significantly lower than that of compound-treated subjects.

TABLE D

| Week | Type of Measurement (all sitting) and Group | Mean Blood Pressures mm Hg | | P-Value of Difference of Means |
|---|---|---|---|---|
| | | Compound-Treated | Placebo-Treated | |
| 0 | Systolic (M & F) | 155.4 | 157.6 | 0.331 |
| 0 | Systolic (F) | 157.2 | 160.6 | 0.016 |
| 0 | Systolic (M) | 154.4 | 155.2 | 0.654 |
| 0 | Diastolic (M & F) | 97.7 | 99.0 | 0.806 |
| 0 | Diastolic (F) | 98.5 | 100.4 | 0.092 |
| 0 | Diastolic (M) | 97.3 | 97.9 | 0.397 |
| 4 | Systolic (M & F) | 143.3 | 150.6 | 0.043 |
| 6 | Systolic (M & F) | 142.9 | 150.3 | 0.041 |
| 2 | Diastolic (M & F) | 92.1 | 96.1 | 0.050 |
| 1 | Systolic (F) | 145.0 | 156.3 | 0.023 |
| 2 | Systolic (F) | 142.5 | 153.4 | 0.042 |
| 4 | Systolic (F) | 140.3 | 153.1 | 0.012 |
| 10 | Systolic (F) | 139.1 | 151.2 | 0.026 |
| 2 | Diastolic (F) | 89.2 | 96.2 | 0.017 |
| 4 | Diastolic (F) | 88.4 | 94.8 | 0.022 |
| 6 | Systolic (M) | 142.5 | 150.5 | 0.023 |

M & F: Male group and female group combined
M: Male Group
F: Female Group

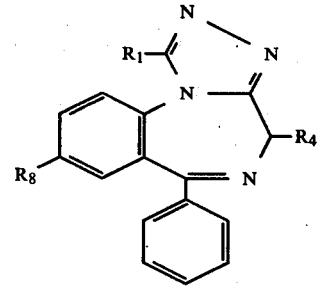

I claim:

1. A method of treating hypertension in mammals which comprises administering to a mammal suffering from said disease an amount of a compound of formula I

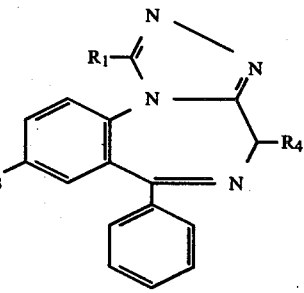

wherein $R_1$ is hydrogen or alkyl of 1 to 3 carbon atoms;
wherein $R_4$ is hydrogen or methyl; and
wherein $R_8$ is hydrogen or halogen;
or a pharmacologically acceptable acid addition salt thereof, effective to reduce the mammal's systemic arterial blood pressure.

2. A method according to claim 1 wherein the compound is one wherein $R_4$ is hydrogen.

3. A method according to claim 2 wherein the compound is one wherein $R_8$ is chlorine, bromine or iodine.

4. A method according to claim 3 wherein the compound is one wherein $R_1$ is alkyl of 1 to 3 carbon atoms.

5. A method according to claim 4 wherein the compound is one wherein $R_1$ is methyl.

6. A method according to any of claims 1 to 5, inclusive, wherein the mammal being treated is a human.

* * * * *